United States Patent [19]

Kuroda et al.

[11] Patent Number: 4,599,432

[45] Date of Patent: Jul. 8, 1986

[54] PROCESS FOR PREPARING A COMPOSITION CONTAINING AN ALKENYL SUCCINIC ANHYDRIDE

[75] Inventors: Katsuhiko Kuroda, Yokohama; Hideki Yamanouchi, Machida, both of Japan

[73] Assignee: Mitsubishi Chemical Industries Ltd., Tokyo, Japan

[21] Appl. No.: 669,081

[22] Filed: Nov. 7, 1984

[30] Foreign Application Priority Data

Nov. 25, 1983 [JP] Japan ................. 58-221820

[51] Int. Cl.$^4$ .......................................... C07D 307/60
[52] U.S. Cl. ................... 549/255; 526/272
[58] Field of Search ................ 549/255; 526/272

[56] References Cited

U.S. PATENT DOCUMENTS

| | | | |
|---|---|---|---|
| 2,542,542 | 2/1951 | Lippincott et al. | 526/272 |
| 3,560,455 | 2/1971 | Hazen | 526/272 |
| 3,706,703 | 12/1972 | Heilman | 524/384 |
| 3,729,451 | 4/1973 | Blecke | 526/203 |
| 3,912,764 | 10/1975 | Palmer, Jr. | 549/255 |

FOREIGN PATENT DOCUMENTS

A663118 10/1965 Belgium .
A2130192 3/1972 France .

OTHER PUBLICATIONS

Kichijima et al., Chemical Abstracts, vol. 85, 161198r (1976).

*Primary Examiner*—Henry R. Jiles
*Assistant Examiner*—Bernard I. Dentz
*Attorney, Agent, or Firm*—Oblon, Fisher, Spivak, McClelland & Maier

[57] ABSTRACT

A process for preparing a composition containing an alkenyl succinic anhydride, which comprises subjecting an olefin and maleic anhydride to a thermal addition reaction, followed by addition of a peroxide to cause unreacted olefin and maleic anhydride to undergo a radical initiated reaction.

13 Claims, No Drawings

4,599,432

PROCESS FOR PREPARING A COMPOSITION CONTAINING AN ALKENYL SUCCINIC ANHYDRIDE

BACKGROUND OF THE INVENTION

1. Field of the Invention

The present invention relates to a process for preparing a composition containing an alkenyl succinic anhydride. More particularly, the present invention relates to a process for preparing a composition containing an alkenyl succinic anhydride and having an excellent hue, from an olefin and maleic anhydride.

2. Description of the Prior Art

An alkenyl succinic anhydride has a wide range of applications in the fields of resin modifiers, plasticizers, dispersing agents, lubricating oil additives or rust-preventing agents. The alkenyl succinic anhydride can readily be prepared by subjecting an olefin and maleic anhydride to a thermal addition reaction at a high temperature of e.g. from 200° to 220° C. However, substantial amounts of unreacted maleic anhydride and olefin remain in the thermal addition reaction product, whereby a purification process is required. As a method of minimizing the unreacted materials, it has been proposed to prolong the reaction time. However, in such a method, a part of maleic anhydride is likely to undergo decomposition, and by-products are likely to form, whereby substantial coloring is likely to result, and the quality of the product will be impaired and the application of the product will be limited. Further, an additional purification process for the removal of the by-products will be required.

Maleic anhydride has a high melting point and is readily sublimated. Accordingly, during the removal of the unreacted materials by heating the above-mentioned reaction product under reduced pressure, the sublimated maleic anhydride is likely to deposit on the inner wall of the piping, whereby a trouble of clogging is likely to be led.

On the other hand, a compound obtained by copolymerizing an olefin and maleic anhydride in the presence of a radical-generating agent, is used in certain fields similar to the fields of application of the alkenyl succinic anhydride. This copolymerization reaction is conducted usually at a temperature of from 90° to 200° C. i.e. substantially lower than the temperature of the thermal addition reaction, whereby the resulting product has a good hue without coloring due to the formation of the by-products. Further, the conversion is generally good, and there is no substantial possibility of the trouble due to the sublimation of maleic anhydride during the removal of the unreacted materials by distillation. However, the compound obtained by this radical reaction is a high polymeric substance having a relatively high viscosity and a relatively high melting point, as compared with the alkenyl succinic anhydride. Accordingly, the compound does not provide the same level of effectiveness as the alkenyl succinic anhydride although it is used in the same fields of application as the alkenyl succinic anhydride.

SUMMARY OF THE INVENTION

The present inventors have conducted extensive researches to solve the above-mentioned problems involved in the production of the alkenyl succinic anhydride and to provide an economical process for preparing an alkenyl succinic anhydride suitable for use in the above-mentioned fields of application. As a result, they have found it possible to substantially reduce unreacted maleic anhydride remaining in the reaction product, by subjecting an olefin and maleic anhydride to a thermal addition reaction and then subjecting the unreacted olefin and maleic anhydride to a radical reaction with an addition of a peroxide, whereby a satisfactory product is obtainable without conducting an additional purification operation, or when the purification operation is conducted to remove volatile materials under reduced pressure, there will be no such a trouble as clogging of the piping due to the deposition of maleic anhydride. The product thereby obtained is not a pure alkenyl succinic anhydride, but a mixture of compounds useful in the same fields of application as the alkenyl succinic anhydride. The product has been found to provide substantially the same level of effectiveness as the alkenyl succinic anhydride when used for the conventional purposes. Further, according to this process, it is not required to raise the conversion so much in the thermal addition reaction, and accordingly, it is possible to lower the reaction temperature and shorten the reaction time, whereby the hue and quality of the product can be substantially improved over the alkenyl succinic anhydride obtained by the conventional process. The present invention has been accomplished based on these discoveries.

Accordingly, it is an object of the present invention to provide a process for economically producing a composition containing an alkenyl succinic anhydride.

Another object of the present invention is to provide an industrially advantageous process for preparing a composition containing an alkenyl succinic anhydride suitable for use in the same fields of application as the alkenyl succinic anhydride.

A further object of the present invention is to provide an industrially advantageous process for preparing a composition containing an alkenyl succinic anhydride having an excellent hue and suitable for use in the same fields of application as the alkenyl succinic anhydride.

Namely, the present invention provides a process for preparing a composition containing an alkenyl succinic anhydride, which comprises subjecting an olefin and maleic anhydride to a thermal addition reaction, followed by a radical reaction with an addition of a peroxide.

DETAILED DESCRIPTION OF THE INVENTION

In the process of the present invention, an olefin and maleic anhydride are subjected to a thermal addition reaction and then to a radical reaction with an addition of a peroxide.

As the olefin which may be employed in the process of the present invention, there may be mentioned compounds having ethylenically unsaturated double bonds in their molecules and having at least 3 carbon atoms, usually from 3 to 10,000 carbon atoms, preferably from 4 to 5,000 carbon atoms, more preferably from 8 to 2,000 carbon atoms. The olefin may be a single substance or a mixture of olefins having different numbers of carbon atoms. Among olefins, an α-olefin is preferred, and a straight-chained α-olefin is more preferred. As the straight-chained α-olefin, an α-olefin having from 12 to 60 carbon atoms obtained by a low polymerization reaction of ethylene, is particularly preferred.

The thermal addition reaction of the olefin with maleic anhydride as the first step of the process, is usually conducted in the absence of a solvent. The temperature for the thermal addition reaction is usually from 170° to 260° C., preferably from 180° to 250° C., more preferably from 190° to 230° C. The reaction time is usually from 30 minutes to 24 hours, preferably from 2 to 12 hours. The molar ratio of the olefin to maleic anhydride to be charged is usually from 1:0.5 to 1:2, preferably from 1:1 to 1:2. The thermal addition reaction is conducted usually until at most 95 mol %, preferably from 30 to 95 mol %, more preferably from 60 to 90 mol %, of the charged maleic anhydride has been reacted. The reaction system is cooled to terminate the thermal addition reaction.

In the radical reaction as the second step, a peroxide is added to the thermal addition reaction product and unreacted maleic anhydride is subjected to a radical reaction. The peroxide to be added to the thermal addition reaction product, may be a usual radical-generating agent such as di-t-butyl peroxide or t-butyl hydroperoxide. The peroxide is added in an amount of from 0.001 to 0.1 mol % relative to the feed olefin. The temperature for the radical reaction is usually from 100° to 260° C., preferably from 130° to 200° C. Substantially all the unreacted maleic anhydride is reacted usually within a period of from 30 minutes to 10 hours.

The composition thus obtained containing an alkenyl succinic anhydride is generally a mixture comprising an adduct of the olefin and maleic anhydride (i.e. an alkenyl succinic anhydride) and a copolymer of the olefin and maleic anhydride.

The reaction for the formation of the alkenyl succinic anhydride is represented by the following formula (I) where R is a hydrogen atom or an alkyl group:

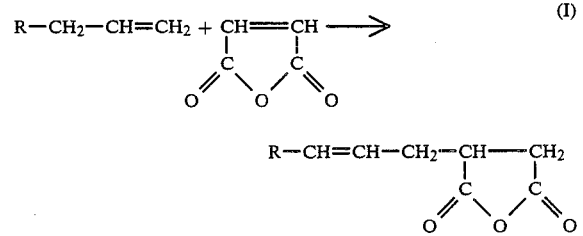

The reaction for the formation of the copolymer of the olefin and maleic anhydride is represented by the following formula (II) where R is as defined above:

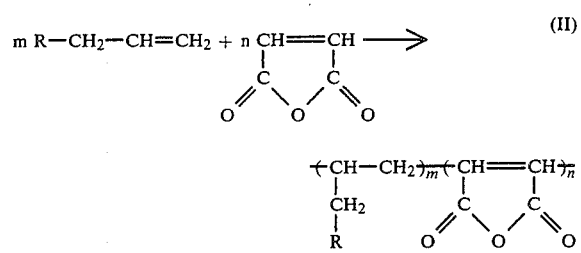

Thus, the ratio of the adduct to the copolymer corresponds substantially to the ratio of the conversion in the thermal addition reaction (i.e. the conversion of maleic anhydride in the thermal addition reaction) to the conversion in the radical reaction.

The composition, usually has a melting point of from −50° to 95° C. and a viscosity of from 10 to 1000 cp at 100° C. For example, when a straight-chained α-olefin having at least 28 carbon atoms is used as the feed olefin, the resulting composition usually has a melting point of from 55° to 95° C. and a viscosity of from 30 to 150 cp at 100° C.

Further, the unreacted maleic anhydride remaining in the reaction product is usually less than 3% relative to the charged amount. While according to the conventional process, the unreacted maleic anhydride remaining in the product caused a trouble during the purification operation, or an attempt to reduce the amount of the remaining unreacted maleic anhydride by a reaction at a high temperature for a long period of time, led to the deterioration of the product, according to the process of the present invention, no substantial amount of unreacted maleic anhydride remains, whereby no trouble during the purification operation is brought about. Further, the hue and quality of the product have been improved, whereby the product can be used advantageously as e.g. a resin modifier, a dispersing agent or a rust-preventing agent.

Now, the present invention will be described in further detail with reference to Examples. However, it should be understood that the present invention is by no means restricted by these specific Examples.

EXAMPLE 1

Into a flask, 650 g (1 mol) of a mixture of α-olefins having from 30 to 60 carbon atoms obtained by low polymerization of ethylene ("DIALEN 30" (trademark) manufactured by Mitsubishi Chemical Industries, Ltd.) and 98 g (1 mol) of maleic anhydride were fed, and after thoroughly flushing with nitrogen gas, reacted at a temperature of 200° C. for 4 hours (thermal addition reaction). The conversion of the maleic anhydride in this reaction was 70%. The reaction mixture was cooled, and 1.46 g (0.01 mol) of di-t-butyl peroxide was added thereto at a temperature of 170° C. Then, the mixture was reacted for 1 hour at a temperature of 170° C. (radical reaction). The conversion of maleic anhydride in this reaction was at least 99%. No substantial formation of colored by-products was observed, and the product had a satisfactory hue and was qualified as a final product without any further purification. The physical properties are shown in Table 1.

COMPARATIVE EXAMPLE 1

Into a flask, 650 g (1 mol) of a mixture of α-olefins having from 30 to 60 carbon atoms obtained by low polymerization of ethylene and 98 g (1 mol) of maleic anhydride, were fed, and after thoroughly flushing with nitrogen gas, reacted at a temperature of 200° C. for 6 hours and then at a temperature of 220° C. for further 2 hours. The conversion of maleic anhydride in this reaction was 85%. Then, it was attempted to remove the maleic anhydride under reduced pressure, whereby the maleic anhydride clogged the piping of the distillate system. Therefore, the maleic anhydride was distilled while the piping for the distillate system was heated and kept warm. The product was substantially colored, and insoluble colored substances deposited in the reactor and precipitated at a lower portion of the product. The physical properties of the product are shown in Table 1.

REFERENCE EXAMPLE 1

Into a flask, 650 g (1 mol) of a mixture of α-olefins having from 30 to 60 carbon atoms obtained by low polymerization of ethylene and 98 g (1 mol) of maleic anhydride were fed, after thoroughly flushing with nitrogen gas, heated to 180° C. Then, 8.76 g (0.06 mol) of di-t-butyl peroxide was added over a period of 2 hours, while carefully watching the heat generation, whereby the radical copolymerization was conducted. After the completion of the addition of the peroxide, the reaction system was kept at 180° C. for 1 hour to complete the reaction. The conversion of the maleic anhydride in this reaction was at least 98%. The hue of the product was good, and the product was qualified as a final product without any further purification. The physical properties are shown in Table 1.

TABLE 1

|  | Viscosity*[1] (cp) | Hue*[2] (Gardner) | Needle*[3] penetration (1/10 mm) | Melting point*[4] (°C.) |
|---|---|---|---|---|
| Example 1 | 50 | 9–10 | 2–3 | 72–76 |
| Comparative Example 1 | 40 | 17–18 | 5 | 72–76 |
| Reference Example 1 | 200 | 2–3 | 3 | 74–76 |

*[1]Viscosity: Measured at 100° C. by means of B-Model Viscometer manufactured by Tokyo Keiki Seizosho K.K.
*[2]Hue: Measured at 100° C. in accordance with ASTM D-1544.
*[3]Needle penetration: Measured at 25° C. in accordance with ASTM D-1321-61T.
*[4]Melting point: Measured by means of an automatic melting point measuring apparatus (METTLER FP manufactured by METTLER INSTRUMENTS AG)

It is apparent from Table 1 that the composition containing an alkenyl succinic anhydride obtained in Example 1 has a low viscosity, and the hue is also substantially improved over the product of Comparative Example 1 representing a conventional process.

EXAMPLE 2

Into a flask, 319 g (1 mol) of a mixture of α-olefins having from 20 to 28 carbon atoms obtained by low polymerization of ethylene ("DIALEN 208" (trademark) manufactured by Mitsubishi Chemical Industries, Ltd.) and 98 g (1 mol) of maleic anhydride, were fed, and after thoroughly flushing with nitrogen gas, reacted at a temperature of 200° C. for 4 hours. The conversion of maleic anhydride in this reaction was 72%. The reaction mixture was cooled, and 1.46 g (0.01 mol) of di-t-butyl peroxide was added at a temperature of 170° C. Then, the mixture was reacted for 1 hour at a temperature of 170° C. The conversion of maleic anhydride in this reaction was at least 98%. A compound having a satisfactory hue as in the case of Example 1 was obtained. The physical properties were measured in the same manner as in Example 1. The results are shown in the following Table.

| Viscosity (cp) | 280 |
|---|---|
| Hue (Gardner) | 6–7 |
| Needle penetration (1/10 mm) | 2–3 |
| Melting point (°C.) | 51–54 |

What is claimed is:

1. A process for preparing a composition containing an alkenyl succinic anhydride, which comprises:
   heating maleic anhydride and an olefin to effect a thermal addition reaction between the reactants; and further
   adding a peroxide to cause unreacted olefin and unreacted maleic anhydride to undergo a radical initiated reaction.

2. The process according to claim 1, wherein the olefin is an α-olefin.

3. The process according to claim 1, wherein the olefin has from 3 to 10,000 carbon atoms.

4. The process according to claim 3, wherein said olefin is a straight chained α-olefin having a carbon atom content of 12 to 60.

5. The process according to claim 1, wherein the thermal addition reaction is conducted until from 30 to 95% of maleic anhydride is reacted.

6. The process according to claim 1, wherein the thermal addition reaction is conducted at a temperature of from 170° to 260° C.

7. The process according to claim 6, wherein said temperature ranges from 180° to 250° C.

8. The process according to claim 1, wherein the starting mole ratio of olefin to maleic anhydride in the thermal addition reaction ranges from 1:0.5 to 1:2.

9. The process according to claim 8, wherein said mole ratio ranges from 1:1 to 1:2.

10. The process according to claim 5, wherein the thermal addition reaction is conducted until from 60 to 90 mole % of the maleic anhydride is reacted.

11. The process according to claim 1, wherein the amount of said peroxide catalyst added in the second step of the process ranges from 0.001 to 0.1 mole % relative to the olefin reactant.

12. The process according to claim 1, wherein the radical catalyzed reaction step occurs at a temperature of 100° to 260° C.

13. The process according to claim 12, wherein said temperature ranges from 130° to 200° C.

* * * * *